United States Patent [19]

Zimmerman et al.

[11] Patent Number: 5,037,838

[45] Date of Patent: Aug. 6, 1991

[54] METHOD FOR THE MANUFACTURE OF TRIETHYLENEDIAMINE USING A PELLETED TITANIA-SUPPORTED TUNGSTOPYROPHOSPHATE CATALYST

[75] Inventors: Robert L. Zimmerman; John F. Knifton, both of Austin, Tex.

[73] Assignee: Texaco Chemical Company, White Plains, N.Y.

[21] Appl. No.: 515,003

[22] Filed: Apr. 26, 1990

[51] Int. Cl.$^5$ .................. A07D 481/08; C07B 35/10; B01J 21/06

[52] U.S. Cl. .................................... 544/352; 502/210

[58] Field of Search ................................. 544/357, 352

[56] References Cited

U.S. PATENT DOCUMENTS 4,757,143  7/1988  Vanderpool ..................... 544/352

Primary Examiner—Mark L. Berch
Attorney, Agent, or Firm—Jack H. Park; Kenneth R. Priem; Carl G. Ries

[57] ABSTRACT

N-hydroxyethyl piperazine is converted to triethylenediamine using a titania-supported tungstopyrophosphate catalyst.

2 Claims, No Drawings

METHOD FOR THE MANUFACTURE OF TRIETHYLENEDIAMINE USING A PELLETED TITANIA-SUPPORTED TUNGSTOPYROPHOSPHATE CATALYST

BACKGROUND OF THE INVENTION

1. Field of the Invention

This invention relates to a catalytic method for the preparation of diazabicyclo-(2.2.2.)-octane (triethylenediamine). More particularly, this invention relates to a catalytic method for the manufacture of triethylenediamine from N-hydroxyethyl piperazine. Still more particularly, this invention is directed to the use of titania-supported tungstopyrophosphate catalysts to catalyze the cyclization of N-hydroxyethyl piperazine to form triethylenediamine. Even more particularly, the present invention is directed a continuous process for the manufacture of triethylenediamine from N-hydroxyethyl piperazine by passing such feedstock over a bed of catalyst in a reaction zone wherein the catalyst is composed of pellets of a titania-supported tungstopyrophosphate catalyst.

2. Prior Art

Vanderpool et al. U.S. Pat. No. 4,806,517 discloses the preparation of linear polyethylene polyamines by reacting ethylenediamine with monoethanolamine in the presence of a group IVB transition metal oxide to which from about 0.5 to 7 wt. % of phosphorus has been thermally chemically bonded.

Knifton et al. U.S. Pat. No. 4,683,335 discloses the use of tungstophosphoric acid or molybdophosphoric acidontitania catalyst for this purpose.

It has heretofore been proposed to manufacture triethylenediamine from a wide variety of cyclic and acyclic polyethylenepolyamines. For example, Brader U.S. Pat. No. 3,157,657 discloses the preparation of triethylenediamine from N-aminoethyl piperazine using a catalyst comprising tungsten or a base modified silica alumina cracking catalyst (see also, Brader U.S. Pat. No. 3,120,526). U.S. Pat. No. 3,080,371 discloses the use of an organic carboxylic acid to catalyze the conversion of hydroxyethyl piperazine to triethylenediamine.

Brader et al. U.S. Pat. No. 3,297,701 discloses a method for the preparation of triethylenediamine by bringing an appropriate feedstock such as a cyclic or acyclic polyethylenepolyamine (e.g., N-aminoethyl piperazine, monoethanolamine, etc.) into contact with a phosphate of an enumerated metal (e.g., aluminum, calcium or iron phosphate). Also, Brader et al. propose the use of 2-(2-hydroxyethoxy) ethylamine as a feedstock for the synthesis of triethylenediamine in U.S. Pat. No. 3,172,891 using an aluminum phosphate catalyst.

Muhlbauer et al. U.S. Pat. No. 3,285,920 is directed to a continuous process for the manufacture of piperazine and triethylenediamine wherein N-aminoethyl piperazine is converted to triethylenediamine using a silica-alumina cracking catalyst alone or modified with alkaline earth metal oxides, alkali metal oxides, zirconia, etc., a tungsten catalyst or a phosphate salt such as a phosphate salt of aluminum or iron.

Vanderpool et al. U.S. Pat. No. 4,757,143 discloses the use of a zirconia on titania support having 0.5 to 7 wt. % of phosphorus bonded thereto for converting a wide variety of cyclic and acyclic hydroxyethyl ethylene polyamines to triethylenediamine.

Vanderpool et al. U.S. Pat. No. 4,754,036 discloses the use of the same class of catalysts for the conjoint manufacture of N-allyl piperazine and 2-methyl triethylenediamine from N-hydroxypropyl piperazine.

SUMMARY OF INVENTION

It has been surprisingly discovered in accordance with the present invention that N-hydroxyethyl piperazine can be converted to triethylenediamine (TEDA) with excellent yields and excellent selectivities per unit of time when using a titania-supported tungstopyrophosphate catalyst containing about 0.5 to about 7 wt. % of phosphorus has been thermally chemically bonded in the form of phosphate linkages and about 0.1 to 30 wt. % of tungsten.

DETAILED DESCRIPTION OF THE EMBODIMENT

Feedstocks

The N-hydroxyethyl derivatives that may be used as feedstocks in accordance with the present invention include compounds having the formula:

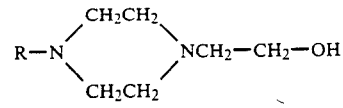

wherein R represents —CH$_2$CH$_2$OH or H, including N-hydroxyethylpiperazine and bis-N-hydroxyethylpiperazine.

Catalysts

The pelleted catalyst compositions of the present invention are normally employed as a fixed bed of catalyst in a continuous reaction system. In a continuous process of this nature, the time of contact of the reactants with the catalyst is one of the interrelated factors that those skilled in the art will adjust, along with temperature, pressure, bed geometry, pellet size, etc. in order to obtain a desired rate of reaction and, hence a desired percentage of conversion of the reactants. In a continuous process, it is not necessary to drive the reaction to completion because unreacted feedstock components can be recycled to the reactor.

It is customary to use cylindrically-shaped catalyst pellets having a diameter essentially equal to the length thereof, such as diameters and lengths ranging from about 0.794 mm (1/32 inch) to about 9.525 mm (⅜ inch). It will be understood that the shape and dimensions of the pellets are not critical to the present invention and that pellets of any suitable shape and dimensions may be used, as desired, by one wishing to practice the process of the present invention.

When cylindrical pellets of catalyst of the type described above are used, the weighted hourly space velocity may be varied within wide limits (e.g., 0.1 to 5 w/hr/w) in order to obtain a desired rate of conversion, as explained above. Normally, space velocities of about 0.5 to 2 w/hr/w will be employed.

Catalyst life is an important factor in conducting a continuous reaction. For example, if a catalyst is easily poisoned, or if catalyst pellets do not have good structural properties, the economics of the process will be seriously and adversely affected.

The catalysts of the present invention are not particularly susceptible to poisoning so this normally does not present a problem. However, under the reaction conditions employed, amines of the type used and formed herein have the potential capability of leaching or otherwise adversely affecting the structural integrity of the pellets. In an extreme instance, catalyst pellets having good initial crush strength and surface hardness will be reduced to fines very rapidly when used under reaction conditions such as those employed herein.

The pelleted catalyst compositions of the present invention are advantageously used in a continuous process for the continuous production of TEDA from N-hydroxyethyl piperazines.

The catalyst compositions of the present invention are prepared by depositing a minor amount of a tungstophosphoric acid on titania. Titania pellets can be prepared by extrusion or by compaction in conventional pelleting apparatus using a pelleting aid such as graphite. It is also within the scope of the present invention to deposit the tungstophosphoric acid on titania followed by pelleting and calcination.

Any appropriate tungstophosphoric heteropoly acid, or a salt thereof, may be used to prepare the catalyst compositions of this invention. Suitable examples include 12-tungstophosphoric acid, having the general formula $H_3[PM_{12}O_{40}]$, where $M=W$, other tungstates having the structure $[P_2M_{18})_{62}]^{6-}$, where the ratio of P to W is 2:18 and $[PM_{11}O_{39}]^{5-}$ where the P:W ratio is 1:11. The heteropoly tungstates may be employed in their acid form or as their salts, such as sodium and potassium 12-tungstophosphate. Both the heteropoly acids and their salts may be used as their hydrates.

The preferred heteropoly phosphotungstate is 12-tungstophosphoric acid. These acids are preferably used in the form of an aqueous solution containing about 1% to about 50% of the acid. It is within the scope of the present invention to use an aqueous solution of two or more tungstophosphoric acids.

As a matter of convenience, the normal practice is to use only one chemical as an acid source.

Preferably the catalyst composition is prepared by impregnating a preformed pellet. A suitable procedure to be used is to immerse titania pellets in an aqueous solution of the acid, preferably at ambient temperature. Higher temperatures of about 100° to about 150° C. can be used, if desired. This treatment should be continued, preferably with agitation, for about 0.1 to about 5 hours sufficient to permit the aqueous solution to penetrate the pores of the titania pellet. Suitably, the amount of aqueous solution of the acid that is used should be adequate to permit full immersion of the titania pellets. Larger amounts of the aqueous solution can be used, if desired, but there is no particular advantage in doing so. At the end of the immersion step, the excess aqueous solution can be evaporated from the treated pellets or the pellets can be removed from the aqueous solution and permitted to dry (e.g., in a drying oven).

Only a minor amount of tungstophosphoric acid will be permanently deposited on the titania pellets by this procedure, such that the treated titania pellets will have only about 0.01 to about 10 wt. % of phosphorus deposited thereon, and normally about 1 wt. % or less (e.g., 0.1 to 1 wt. %). A small but significantly larger percentage of tungsten will be co-deposited on the titania, such as about 0.1 to about 30 wt. %, and normally from about 1 to about 10 wt. % of tungsten.

It will be understood that the phosphorus and tungsten that are present on thus-treated titania pellets are not present as elemental compounds, but rather as tungstophosphorus groups that are chemically bound, normally as an oxide, to the titania support. The exact nature of the bonding is not completely understood.

The pelleted catalyst compositions of the present invention should be calcined. They can be calcined prior to use or calcined in situ when used as catalysts at temperatures in excess of about 100° C. When the catalysts are to be calcined prior to use, calcination is suitably conducted for 2 to 24 hours at a temperature of 100° C. but below the temperature at which thermal destruction of the chemical bonding occurs. This can be determined by routine experimentation for a particular catalyst. Temperatures above 900° C. should be avoided. A suitable calcining temperature range is normally 200° to 800° C. and, more preferably, 300° to 600° C.

Alternatively, the titania can be treated in powdered form with the aqueous acidic solution and the powder can thereafter be pelleted. If the pelleting treatment is conducted at a temperature of about 100° C. or more, thermal activation will normally have been obtained and it will not be absolutely necessary to perform a calcining operation before use. If lower treating temperatures are used, calcining is normally a desired operation before use. The calcining operation can be conducted prior to or subsequent to the pelleting step.

In any event, in-situ calcining will occur when the pelleted compositions are used to catalyze the reaction of monoethanolamine with ethylenediamine at 250° to 400° C.

Reaction Conditions

The reaction of the present invention is suitably conducted at a temperature of about 250°–400° C. and, more preferably, at a temperature of about 300° to about 350° C.

The reaction is also preferably conducted at atmospheric pressure. Superatmospheric or subatmospheric pressures may be utilized if desired, but there is no particular advantage in doing so.

When the reaction is conducted on a continuous basis, the feedstock may suitably be passed over a bed of pelleted catalyst at a liquid hourly space velocity (1 hsv) of about 0.1 to about 10 volumes of the aqueous solution of the amine feedstock per volume of catalyst per hour. More preferably, the 1 hsv will be from about 0.5 to about 2.

It is not necessary to use either ammonia or hydrogen as feed components in the practice of the process of the present invention.

Recovery and Purification

The product of the present invention, triethylenediamine, is a compound having the formula:

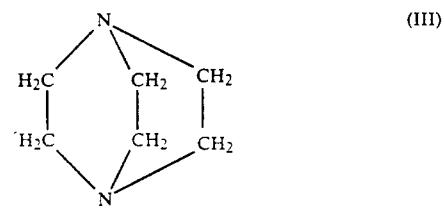

(III)

Triethylenediamine in its pure form is a hygroscopic crystalline solid having a melting point of about 158°–160° C. Triethylenediamine is sparingly soluble in glycols such as ethylene glycol, propylene glycol, diethylene glycol, dipropylene glycol, etc. Also, when an aqueous reaction product containing triethylenediamine and propylene glycol is distilled, the triethylene diamine and propylene glycol can be distilled overhead as a triethylene diamine-propylene glycol azeotrope, thereby resulting in the recovery of a purified material in liquid form. This has the advantage of avoiding the necessity of recovering the triethylenediamine as a hygroscopic crystalline solid with all of the processing problems that are entailed in the handling of hygroscopic crystalline solids.

EXAMPLES

Equipment and Procedures

In all cases, these evaluations were performed in a 100 cc reactor constructed of ½ inch stainless steel tubing 17 inches long connected to a ⅛ inch feed and effluent lines with swagelok fittings. The reactor tube was situated inside of a 3×3 inch aluminum block which was heated electrically with four 1000 watt strip heaters. Temperature control was achieved with a Thermoelectric controller monitoring thermocouples attached to the skin of the reactor body. The feed was charged to the reactor system with a Beckman 110 A L.C. pump. For safety, pressure relief was provided by a 3000 lb. rupture disk assembly although all runs were preformed at atmospheric pressure to minimize bimolecular reactions. The reactor effluent was collected in a glass jug and sampled after the system had lined-out at the proscribed temperature for at least 2.5 hours.

In general the feedstock consisted of a 4:1 aqueous feed. For example, HEP feed consisted of 4 parts water by weight and 1 part HEP by weight.

Analysis of the reactor effluent was achieved using an OV-17 column in a Hewlett-Packard 5710A gas chromatograph. Analysis was on a water-free and feed-free basis. Since the conversion of HEP and BisHEP were nearly quantitative, the selectivities were close to calculated yields.

I. Prior Art Reactions

N-Hydroxyethyl Piperazine (HEP) Feedstock and Prior Art Catalyst

The catalyst that was used was prepared from pelleted titania and polyphosphoric acid. It had about 2 wt. % of phosphorus thermally chemically bonded thereto and was prepared by dipping the preformed pellets into a 30% polyphosphoric acid solution, followed by decanting and calcining at 450° C.

As described above, a 20 wt. % aqueous HEP solution was charged to the reactor with the results shown below. In this experiment, the purpose of the water is to further minimize bimolecular reactions that would be expected to result in the dimerization and polymerization of the HEP by acting as an inert diluent. In larger reactor systems water may be necessary as a heat transport medium. It must be emphasized that these selectivities are only approximate due to the nature of G.C. analysis.

Data is presented in Table I.

TABLE I[a]

| Ex. | TEMP[b] | TEDA via HEP | | | | |
| --- | --- | --- | --- | --- | --- | --- |
|  |  | Conv. | TEDA | PIP | EtPIP | Hvs[c] |
| 1 | 298 | 36 | 66 | 3.6 | 1.3 | 15 |
| 2 | 311 | 86 | 83 | 4.2 | 3.4 | 7 |
| 3 | 320 | 100 | 88 | 5.8 | 6.0 | <1 |
| 4 | 330 | 100 | 83 | 7.1 | 9.3 | <1 |
| 5 | 337 | 100 | 75 | 8.0 | 13.6 | <1 |

[a]Data is basis GC analysis of crude reactor effluents. Selectivities are approximate Area % on a water and feed free basis.
[b]Temperature in degrees Centigrade.
[c]Heavies are probably dimers of HEP.

The interpretations are:
1. Increased temperatures increase byproduct formation and result in further reaction of an unidentified heavy by-product to give additional TEDA, piperazine and N-ethylpiperzine.
2. Selectivity to the desired TEDA is optimized at the minimum temperature required for 100% HEP conversion.
3. The heavy byproducts are apparently convertible to TEDA.

II. Tungstophosphoric Acid Titania Catalyst Preparations

A series of pelleted catalysts were prepared by depositing tungstophosphoric acid on a titania support.

EXAMPLE 1

Preparation of 12-Tungstophosphoric Acid-on-Titania (5972-62)

To a 125-cc of titania extrudates (⅛" extrudates, 51 m²/g surface area, provided by the Norton Company) is added a solution of 10.0 g of 12-tungstophosphoric acid in 50 ml of water. The mixture is stirred to absorb the liquid into the pores of the solid, excess liquid is recovered by slow rotary evaporation, and 127.5 g of white extrudates are isolated.

Analysis of the extrudates shows the presence of 0.13% phosphorus and 5.4% tungsten.

EXAMPLES 2-7

Additional 12-Tungstophosphoric Acid on Titania Catalysts

The procedure of Example 1 was repeated using ⅛" titania extrudates impregnated with differing quantities of tungstophosphoric acid. The amount (in grams) of tungstophosphoric acid used and the amount of tungsten and phosphorus deposited on the titania pellets is set out below:

| Example | Weight (gms) of Tungstophosphoric Acid Used | % of Phosphorus Deposited | % of Tungsten Deposited |
| --- | --- | --- | --- |
| 2[1] | 10.0 | 0.1 | 6.0 |
| 3[2] | 20.0 | 0.2 | 9.5 |
| 4[2] | 40.0 | 0.4 | 17.5 |
| 5[3] | 10.0 | (a) | 3.8 |
| 6[2] | 5.0 | (a) | 3.0 |
| 7[3] | 20.0 | (a) | 6.7 |

[1]125 ml of pellets having a surface area of 120 m²/g.
[2]125 ml of pellets having a surface area of 51 m²/g.
[3]125 ml of pellets having a surface area of 60 m²/g.
(a) Not determined.

I. Preparation of Catalyst

To 125 cc of MSA titania extrudates (⅛" extrudates, 51 m²/g surface area, provided by the Norton Co.) was added a solution of 5.0 g of 12-tungstophosphoric acid in 50 ml of water. The mixture was stirred to absorb the liquid into the pores of the solid. Excess liquid was recovered by slow rotary evaporation. White solid extrudates (122.8 g) were isolated. Analysis of the dried extrudates showed the following: 3.0% tungsten, 0.1% phosphorus. N.B. #5972-86 II. In the following examples 100 cc of catalyst were charged to a tubular reactor. The reactor was then heated to the desired temperature and then the reaction feed was fed to the reactor. A down flow mode was used and all reactions were done at atmospheric pressure.

TABLE II

TRIETHYLENE DIAMINE FROM CRUDE HYDROXYETHYL PIPERAZINE

| Catalyst | Feed | Temp. °C. | Space Velocity | Conversion HEP | BISHEP | Select. TEDA % | Yield TEDA % | Grams TEDA/Hr |
|---|---|---|---|---|---|---|---|---|
| Phosphoric | Crude HEP[1] | 300 | 1 | 44 | 63 | 71 | | |
| on Titanium | | 311 | 1 | 65 | 82 | 77 | | |
| Oxide | | 323 | 1 | 99 | 100 | 79 | | |
| | | 331 | 1 | 98 | 100 | 80 | 69 | 8.8 |
| | | 300 | 0.5 | 95 | 95 | 80 | | |
| | | 310 | 0.5 | 98 | 100 | 79 | | |
| | | 280 | 0.5 | 37 | 67 | 82 | | |
| | | 290 | 0.5 | 42 | 65 | 75 | | |
| | | 306 | 0.47 | 97 | 100 | 75 | 69 | 4.2 |
| Aluminum | Crude HEP[1] | 240 | 1 | 1 | 7 | 54 | | |
| Phosphate | | 260 | 1 | 5 | 26 | 87 | | |
| on Alumina | | 280 | 1 | 17 | 41 | 71 | | |
| | | 300 | 1 | 44 | 78 | 72 | | |
| | | 320 | 1 | 90 | 100 | 74 | | |
| | | 340 | 0.84 | 97 | 100 | 88 | 81 | 8.7 |
| Catalyst | Crude HEP[1] | 310 | 0.9 | 94 | 100 | 83 | 70 | 8.1 |
| Example I | | 320 | 0.88 | 85 | 100 | 72 | | |
| | | 343 | 0.87 | 100 | 100 | 82 | | |
| | | 340 | 1.54 | 100 | 100 | 75 | | |
| | | 340 | 1.76 | 100 | 100 | 78 | | |
| | | 340 | 1.95 | 100 | 100 | 80 | | |
| | | 340 | 2.5 | 95 | 100 | 80 | 58 | 17.4 |
| | | 331 | 2.52 | 78 | 100 | 82 | | |
| | | 331 | 2.28 | 83 | 100 | 82 | 74 | 20 |
| Catalyst | BISHEP[2] | 312 | 2.11 | | 73 | 78 | | |
| Example I | | 312 | 2.05 | | 85 | 85 | | |
| | | 331 | 2.02 | | 89 | 90 | | |
| Aluminum | BISHEP[2] | 320 | 0.4 | | 100 | 87 | | |
| Phosphate on Alumina | | 320 | 0.88 | | 98 | 97 | | |

[1] 18.6% of crude HEP (18.5% piperazine, 53.9% hydroxyethyl piperazine and 27.6% bishydroxyethyl piperazine), 81.4% water.
[2] 20% bishydroxyethyl piperazine, 80% water.

As can be easily seen in the example the catalyst of Example I produces by far the greatest amount of TEDA per hour. It also gives yield comparable to aluminum phosphate and strontium phosphate and far better than phosphoric acid on titanium oxide.

The foregoing examples are given by way of illustration only and are not intended as limitations on the scope of this invention, as defined by the appended claims.

What is claimed is:

1. A method for the manufacture of triethylenediamine which comprises bringing an aqueous solution containing about 5 to about 50 wt. % of a N-hydroxyethyl piperazine feedstock into contact with a titania-supported tungstopyrophosphate catalyst cyclization catalyst at a temperature of about 300°-400° C. for a period of time sufficient to convert at least a portion of said feedstock to triethylenediamine, said feedstock having the formula:

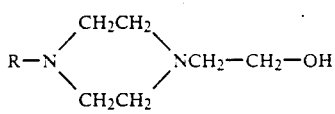

wherein R represents —CH$_2$CH$_2$OH or hydrogen.

2. A method for the continuous manufacture of triethylenediamine which comprises forming an aqueous solution of a N-hydroxyethyl piperazine feedstock containing from about 5 to about 50 wt. % of said N-hydroxyethyl piperazine, continuously bringing said aqueous solution into contact with a pelleted cyclization catalyst at a temperature within the range of about 300° to about 400° C. at a liquid hourly space velocity of about 0.5 to about 5 sufficient to substantially completely convert said feedstock into reaction products including triethylenediamine, continuously recovering an aqueous solution of said reaction product and continuously recovering triethylene diamine therefrom, a. said pelleted cyclization catalyst consists essentially of titania-supported tungstopyrophosphate catalyst having from about 0.5 to about 7 wt. % of phosphorus thermally chemically bonded to the surface thereof in the form of phosphate bonds, b. said feedstock having the formula:

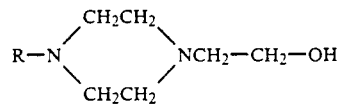

wherein R represents —CH$_2$CH$_2$OH or hydrogen.

* * * * *